United States Patent [19]
Krantz et al.

[11] Patent Number: 6,107,489
[45] Date of Patent: Aug. 22, 2000

[54] EXTENDED LIFETIMES IN VIVO RENIN INHIBITORS

[75] Inventors: Alexander Krantz, San Mateo, Calif.; Dominique Blanchard, Nantes, France; Diane DeNagel; Yonghong Song, both of Foster City, Calif.

[73] Assignee: ConjuChem, Inc., Montreal, Canada

[21] Appl. No.: 09/267,274

[22] Filed: Mar. 12, 1999

Related U.S. Application Data

[60] Provisional application No. 60/078,230, Mar. 17, 1998, abandoned.

[51] Int. Cl.⁷ .......................... C07D 233/54; A61K 38/05
[52] U.S. Cl. ..................................... 548/338.1; 548/335.1; 514/19; 514/18; 530/330; 530/331
[58] Field of Search ................................ 514/17, 19, 18; 530/330, 331; 548/338.1, 335.1

[56] References Cited

U.S. PATENT DOCUMENTS

| | | | |
|---|---|---|---|
| 5,612,034 | 3/1997 | Pouletty et al. | 530/402 |
| 5,681,811 | 10/1997 | Ekwuribe | 514/8 |
| 5,705,143 | 1/1998 | Bower et al. | 530/300 |
| 5,840,733 | 11/1998 | Krantz et al. | 514/311 |
| 5,843,440 | 12/1998 | Pouletty et al. | 424/133.1 |

FOREIGN PATENT DOCUMENTS 0 312 158 A2  4/1989  European Pat. Off. .

OTHER PUBLICATIONS

The Merck Index, Budavari Editor, 12th ed., Merck & Co., Inc. Whitehouse Station, N.J. Entry No. 1272, 3209, 3210, 1996.

*Primary Examiner*—F. T. Moezie
*Attorney, Agent, or Firm*—Limbach & Limbach LLP

[57] ABSTRACT

Novel compounds comprising chemically reactive intermediates which can react with available reactive functionalities on blood components to form covalent linkages, where the resulting covalently-bound conjugates are found to have renin inhibition activity are provided. Specifically, the renin inhibitor compounds of the present invention are tripeptide derivatives of a known renin inhibitor which can be covalently linked to chemically reactive functionalities on various blood components. The conjugated renin inhibitors thereby have extended lifetimes in the bloodstream, as compared to the unconjugated parent drug, and are, therefore, capable of maintaining renin inhibitory activity for extended periods of time as compared to the unconjugated parent drug. Also provided herein are methods for inhibiting renin activity in vivo comprising administering to the bloodstream of a mammalian host the novel compounds of the present invention.

15 Claims, 5 Drawing Sheets

| Derivative | R₁ Group | n | R₂ Group | IC₅₀ |
|---|---|---|---|---|
| YS-004-24 | t-Boc | 11 | H | 700 nM |
| YS-004-36 | Biotin | 11 | H | 5000 nM |
| YS-004-39 | Biotin | 11 | NHS | ND |
| YS-004-40 | t-Boc | 11 | NHS | ND |
| YS-004-54 | t-Boc | 5 | NH₂ | ND |
| YS-004-63 | t-Boc | 5 | CH₃ | 100 nM |
| YS-004-65 | t-Boc | 5 | H | 50 nM |
| YS-004-69 | t-Boc | 5 | NHS | ND |
| YS-018-01 | Biotin | 5 | H | 250 nM |
| YS-018-03 | Biotin | 5 | Sulfo-NHS | ND |
| YS-018-05 | t-Boc | 5 | Sulfo-NHS | ND |
| YS-018-06 | Biotin | 5 | NHS | ND |

EXTENDED LIFETIMES IN VIVO RENIN INHIBITORS

RELATED APPLICATION

This application claims the benefit under 35 U.S.C. § 119(e) of U.S. Provisional Patent Application No. 60/078,230 filed Mar. 17, 1998 now abandoned.

TECHNICAL FIELD

The field of this invention is the extended lifetime of physiologically active agents in a mammalian host, more specifically, the extended lifetime of inhibitors of renin activity in a mammalian host.

BACKGROUND OF THE INVENTION

The administration of physiologically active substances to a mammalian host is a complicated matter which requires the consideration of numerous factors for in vivo efficacy. For example, for a physiologically active substance to be therapeutically effective in vivo, it must be able (in most situations) to bind to a specific target molecule, so as to inhibit or activate the physiological activity of that target molecule. Binding to a target molecule, however, requires that the physiologically active substance either be capable of direct administration at the target site or be capable of being administered elsewhere and subsequently transported to the target site without significant loss of therapeutic activity. Unfortunately, various problems arise in the administration and transport of physiologically active substances in mammals.

For example, many therapeutic drugs are often administered orally or intravascularly. In the case of oral administration, for a drug to effectively reach the target site, the drug must not only survive the degradative processes associated with the mammalian gastrointestinal tract, but it must also be transported from the gastrointestinal tract into the host's vascular system. The problems associated with oral drug administration, therefore, often result in a significant reduction in in vivo therapeutic activity which, in turn, results in the presence of subtherapeutic doses of the drug for extended periods of time.

Unlike oral administration, when a drug is administered intravascularly, it is not subject to the degradative effects of the gastrointestinal tract nor the need for transport from the gastrointestinal tract into the vascular system. However, when administered intravascularly, drugs are still often subject to being confined to a compartment other than the region where the target site is, being eliminated through the degradative and excretory processes of the liver and kidneys and, depending upon the nature of the drug, being subject to the lymphocytic system.

Furthermore, in addition to the problems associated with degradation and transport of administered drugs in mammals, in order to provide for an effective therapeutic effect, one must also maintain a therapeutically effective amount of the drug in the vascular system over an extended period of time, where the drug is available for binding to the target. Unfortunately, however, many drugs are often poorly absorbed from the gastrointestinal tract and/or are rapidly cleared from the host's bloodstream, thereby resulting in severe limitations for the clinical applications of such drugs.

In attempts to overcome many of the problems associated with drug degradation and transport as well as attempting to maintain effective drug concentrations over extended periods of time, various drug administration regimens have been developed. For example, one common administration technique is giving a large bolus of the drug at periodic time intervals. This manner of administration, however, often results in subtherapeutic doses of the drug for extended periods of time followed by doses which may greatly exceed the desired therapeutic level. The latter may often involve serious adverse side effects.

Other efforts to avoid the problems associated with giving boluses have, in part, involved providing depots comprising the drug. For example, various pumps and biodegradable and non-biodegradable capsules have been devised for the delivery of drug over an extended period of time. These devices, however, also have a variety of shortcomings in their profile of drug delivery, for example, often resulting in an inflammatory response and/or being subject to interference in their release of active drug.

One class of drugs which is subject to many of the problems described above are those drugs that serve to inhibit the activity of the mammalian enzyme, renin. Such drugs function to inhibit endogenous renin activity, thereby affecting blood volume, pressure and the electrolyte balance of body fluids. The clinical application of these drugs, however, is severely limited by the fact that they are often poorly absorbed from the gastrointestinal tract and/or are rapidly cleared from the host's bloodstream.

There is, therefore, substantial interest in being able to provide for improved methods of providing for the continued maintenance of renin inhibitors in the bloodstream. The method as described herein involves the covalent linking of derivatized renin inhibitors to blood components for the purpose of enhancing the lifetime of the renin inhibitors in the vascular system. Although derivatized, the renin inhibitors retain activity when covalently bound to a blood component and provide renin inhibitory activity over an extended period of time as compared to that obtained with unconjugated drug.

SUMMARY OF THE INVENTION

Novel compounds are provided comprising chemically reactive intermediates which can react with available reactive functionalities on blood components to form covalent linkages, where the resulting covalently-bound conjugates are found to have renin inhibition activity. Specifically, the compounds of the present invention are tripeptide derivatives of a known renin inhibitor which can be covalently linked to chemically reactive functionalities on various blood components. The conjugated renin inhibitors thereby have extended lifetimes in the bloodstream, as compared to the unconjugated parent drug, and are, therefore, capable of maintaining renin inhibitory activity for extended periods of time as compared to the unconjugated parent drug.

Also provided herein are methods of synthesizing the derivatized renin inhibitors of the invention.

Also provided herein are methods for inhibiting renin activity in vivo comprising administering to the bloodstream of a mammalian host the novel compounds of the present invention. The compounds of the present invention may also be reacted with blood or blood proteins ex vivo to form treated blood and treated blood proteins prior to administration of the treated blood or treated blood proteins to a host.

DESCRIPTION OF THE SPECIFIC EMBODIMENTS

To ensure a complete understanding of the invention, the following definitions are provided:

Renin Inhibitor Peptides: Renin Inhibitor peptides are peptides comprised of amino acids that inhibit the activity of the mammalian enzyme renin.

Renin: Renin is an aspartyl protease that attacks several natural substrates like $\alpha_2$-globulin angiotensinogen. Renin is a principal component in the homeostatic regulation of blood volume and pressure and of the electrolyte composition of body fluid.

Reactive Entities: Reactive entities are entities capable of forming a covalent bond. Such reactive agents are coupled or bonded to renin inhibitor peptide of interest. Reactive entities will generally be stable in an aqueous environment and will usually be carboxy, phosphoryl, or convenient acyl group, either as an ester or a mixed anhydride, or an imidate, thereby being capable of forming a covalent bond with functionalities such as an amino group, a hydroxy or a thiol at the target site on mobile blood components. For the most part, the esters will involve phenolic compounds, or be thiol esters, alkyl esters, phosphate esters, or the like.

Functionalities: Functionalities are groups on blood components including mobile proteins or renin inhibitor peptide derivatives to which reactive entities react to form covalent bonds. Functionalities include hydroxyl groups for bonding to ester reactive entities; thiol groups for bonding to imidates and thioester groups; amino groups for bonding to carboxy, phosphoryl or acyl groups on reactive entities and carboxyl groups for bonding to amino groups Mobile Blood Proteins: Mobile blood proteins are soluble blood proteins. These blood proteins are not membrane-associated, are present in the blood for extended periods of time and are present in a minimum concentration of at least 0.1 μg/ml. Mobile blood proteins include serum albumin, transferrin, ferritin and immunoglobulins such as IgM and IgG. The half-life of mobile blood proteins in the blood stream is at least about 12 hours.

Protective Groups: Protective groups are chemical moieties utilized to protect renin inhibitor peptide derivatives from reacting with themselves. Various protective groups are disclosed in U.S. Pat. No. 5,493,007 which is hereby incorporated by reference. Such protective groups include acetyl, fluorenylmethyloxycarbonyl (Fmoc), Boc, Cbz, and the like.

Linking Groups: Linking groups are chemical moieties that link or connect reactive entities to renin inhibitor peptides. Linking groups may comprise one or more alkyl groups, alkoxy groups, alkenyl group, alkynyl groups or amino group substituted by alkyl groups, cycloalkyl groups, polycyclic groups, aryl groups, polyaryl groups, substituted aryl groups, heterocyclic groups, and substituted heterocyclic groups.

Taking into account these definitions, the present invention is directed to methods and compositions for the treatment of patients having vascular and/or cardiac disorders by inhibiting angiotensin II formation through inhibition of the enzyme, renin. The method employs a novel renin inhibitor compound comprising a tripeptide derivative of a known renin inhibitor, wherein the novel compound has a chemically reactive group that reacts with available reactive functionalities on various blood components, thereby covalently bonding the renin inhibitor to those blood components. Therefore, through the covalent bonding of the derivatized renin inhibitor to long-lived blood components, the effective lifetime of the renin inhibitor in the host's vascular system is greatly increased.

The various sites with which the chemically reactive group of the derivatized renin inhibitor molecule may react include cells, particularly red blood cells (erythrocytes) and platelets, and proteins, such as immunoglobulins, including IgG and IgM, serum albumin, ferritin, steroid binding proteins, transferrin, thyroxin binding protein, $\alpha$-2-macroglobulin, and the like. Those proteins with which the derivatized renin inhibitor compound reacts, which are not long-lived, will generally be eliminated from the host within about three days, so that the proteins indicated above (including the proteins of the cells) will remain at least three days, usually at least four days, and may remain five days or more, usually not exceeding 60 days, more usually not exceeding 30 days, particularly as to the half life, based on the concentration in the blood, as measured in from about 1–3 hours after administration.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

The derivatized renin inhibitor compounds of the present invention will, for the most part, have the following formula:

wherein:

R$_1$ is an acyl group of from 1–10 carbon atoms, more usually of from 1–8 carbon atoms, preferably of from about 2–6 carbon atoms, and includes alkoxy carbonyl, where the alkyl group is of 1–5 carbon atoms, more usually of from 2–4 carbon atoms, particularly t-butyloxycarbonyl, formyl, acetyl, propionyl, butyryl, methoxyacetyl, pivaloyl, and the like;

Y is a linking group of from 2–30, more usually of from 2–12, preferably of from 4–12 atoms, particularly carbon, oxygen, phosphorous and nitrogen, more particularly carbon and oxygen, where the oxygen is preferably present as oxy ether, where Y may be alkylene, oxyalkylene, or polyoxyalkylene, where the oxyalkylene group has from 2–3 carbon atoms, and the like;

Z is an active functionality or precursor to an active functionality, such as carboxy, carboxy ester, where the ester group is of 1–8, more usually 1–6 carbon atoms, particularly a physiologically acceptable leaving group which activates the carboxy carbonyl for reaction with amino groups in an aqueous system, e.g., N-hydroxysuccinimide (NHS), N-hydroxysulfosuccinimide, (sulfo-NHS), maleimide-benzoyl-succinimide (MBS), gamma-maleimido-butyryloxy succinimide ester (GMBS) and maleimidopropionic acid (MPA), N-hydroxysuccinimide isocyanate, thiolester, thionocarboxylic acid ester, imino ester, mixed anhydride, e.g. carbodiimide anhydride, carbonate ester, etc. and the like; and a is 0 or 1, usually 1.

Alternatively, $R_1$ may be a marker for identification and analysis, so that $R_1$ may include a hapten, such as biotin, digoxin, digoxigenin, or the like.

The reactive functionalities which are available on proteins for covalently bonding to the chemically reactive group of the derivatized renin inhibitor molecule are primarily amino groups, carboxyl groups and thiol groups. While any of these may be used as the target of the chemically reactive group on the renin inhibitor, for the most part, bonds to amino groups will be employed, particularly with formation of amide bonds. To form amide bonds, one may use as a chemically reactive group a wide variety of active carboxyl groups, particularly esters, where the hydroxyl moiety is physiologically acceptable at the levels required. While a number of different hydroxyl groups may be employed, the most convenient will be N-hydroxysuccinimide (NHS) and N-hydroxy sulfosuccinimide, (sulfo-NHS) maleimide-benzoyl-succinimide (MBS), gamma-maleimido-butyryloxy succinimide ester (GMBS) and maleimidopropionic acid (MPA), although other reactive groups, which are functional in an aqueous medium such as blood, may also be employed. In some cases, special reagents find use, such as azido, diazo, carbodiimide anhydride, hydrazine, dialdehydes, thiol groups, or amines to form amides, esters, imines, thioethers, disulfides, substituted amines, or the like. Usually, the covalent bond which is formed should be able to be maintained during the lifetime of the blood component, unless it is intended to be a release site. In the preferred embodiments of this invention, the functional group on this protein will be a thiol group and the chemically reactive group will be a maleimido-containing group such as (GMBA or MPA). GMBA stands for gamma-maleimide-butrylamide.

The parent renin inhibitor upon which the derivatized inhibitors of the present invention are based has an $IC_{50}$ of between about 4–19 nM. The derivatized renin inhibitors of the present invention will generally have substantially lower $IC_{50}$'s, generally in the range of about 0.5–0.01 of the $IC_{50}$ of the parent molecule. Desirably, the $IC_{50}$ should be not less than 0.05, preferably not less than about 0.1. In view of the varying $IC_{50}$'S, the amount of the derivatized renin inhibitor administered will also vary.

If desired, the subject conjugates may also be prepared ex vivo by combining blood with a derivatized renin inhibitor molecule of the present invention and then returning the conjugated blood to the host. Moreover, the above may also be accomplished by first purifying an individual blood component or limited number of components, such as red blood cells, blood proteins, immunoglobulins, serum albumin, or the like, and combining the component or components ex vivo with the chemically reactive renin inhibitory compound. The functionalized blood or blood component may then be returned to the host to provide in vivo the subject therapeutically effective conjugates. The blood also may be treated to prevent coagulation during handling ex vivo.

When conjugates are prepared ex vivo, the ratio of derivatized renin inhibitor molecules to blood components will vary widely, depending upon whether whole blood or just a purified component is used as a bonding site for the derivatized renin inhibitor.

Derivatives of renin inhibitor peptides and their analogs which can conjugate with proteins and other mobile blood proteins are prepared by the use of linking groups having chemically reactive groups which covalently bond to reactive functionalities on proteins. Specific synthetic pathways are outlined in the Examples section.

Specific Labeling

Preferably, the renin inhibitor peptides of this invention are designed to specifically react with thiol groups on mobile blood proteins. Such reaction is preferably established by covalent bonding of a maleimide link (e.g. prepared from GMBS, MPA or other maleimides) to a thiol group on a mobile blood protein such as albumin or IgG.

Under certain circumstances, specific labeling with maleimides offers several advantages over non-specific labeling of mobile proteins with groups such as NHS and sulfo-NHS. Thiol groups are less abundant in vivo than amino groups. Therefore, the maleimide renin inhibitor peptide derivatives of this invention will covalently bond to fewer proteins. For example, in albumin (the most abundant blood protein) there is only a single thiol group. Thus, renin inhibitor-maleimide-albumin conjugates will tend to comprise approximately a 1:1 ratio of renin inhibitor peptide derivatives to albumin. In addition to albumin, IgG molecules (class II) also have free thiols. Since IgG molecules and serum albumin make up the majority of the soluble protein in blood they also make up the majority of the free thiol groups in blood that are available to covalently bond to maleimide-renin inhibitor peptide derivatives.

Through controlled administration of maleimide-renin inhibitor peptides in vivo, one can control the specific labeling of albumin and IgG in vivo. In typical administrations, 80–90% of the administered maleimide-renin inhibitor peptide will label albumin and 10–20% will label IgG. Trace labeling of free thiols such as glutathione will also occur. Such specific labeling is preferred for in vivo use as it permits an accurate calculation of the estimated half-life of the administered agent.

In addition to providing controlled specific in vivo labeling, maleimide-renin inhibitor peptides can provide specific labeling of serum albumin and IgG ex vivo. Such ex vivo labeling involves the addition of maleimide-renin inhibitor to blood, serum or saline solution containing serum albumin. Once modified ex vivo with renin inhibitor-Mal, the blood, serum or saline solution can be readministered to the blood for in vivo treatment.

In contrast to NHS-peptides, maleimide-renin inhibitor peptides are generally quite stable in the presence of aqueous solutions and in the presence of free amines. Since maleimide renin inhibitor derivatives will only react with free thiols, protective groups are generally not necessary to prevent the maleimide-renin inhibitor peptide derivative from reacting with itself. In addition, the increased stability of the peptide permits the use of further purification steps such as HPLC to prepare highly purified products suitable for in vivo use. Lastly, the increased chemical stability provides a product with a longer shelf life.

Non-Specific Labeling

Under some circumstances, non-specific labeling of blood proteins with renin inhibitor peptides is desirable. Bonds to free amino groups can be employed, particularly with the formation of amide bonds for non-specific labeling. To form such bonds, one may use as a chemically reactive group a wide variety of active carboxyl groups, particularly esters, where the hydroxyl moiety is physiologically acceptable at the levels required. While a number of different hydroxyl groups may be employed in these linking agents, the most convenient would be N-hydroxysuccinimide (NHS) and N-hydroxy-sulfosuccinimide (sulfo-NHS).

Other linking agents which may be utilized are described in U.S. Pat. No. 5,612,034, which is hereby incorporated herein.

The various sites with which the chemically reactive group of the subject non-specific renin inhibitor peptide derivatives may react in vivo include cells, particularly red blood cells (erythrocytes) and platelets, and proteins such as immunoglobulins, including IgG and IgM, serum albumin, ferritin, steroid binding proteins, transferrin, thyroxin binding protein, α-2macroglobulin and the like.

The choice of the long lived blood component will be affected by the purpose for binding to the target. Thus, depending on the choice of the long lived blood component, the target may be rapidly segregated and excreted from the body, segregated in a biologically inactive form to be slowly eliminated, or degraded over time. The long lived blood component will normally be mobile in the vascular system, having a substantially uniform or variant distribution in the vascular system, where the long lived blood component may be preferentially present in particular compartments, including solid tissue. The choice of long lived blood component will also depend in part on the nature of the target. For instance, red blood cells are preferred for cellular pathogenic agents for efficient clearance.

A long lived blood component has a half life of at least about 12 hours, usually at least about 48 hours, preferably at least about 5 days, desirably at least about 10 days and more desirably at least about 20 days or more. Generally, half lives are determined by serial measurements of whole blood, plasma or serum levels of the compound following labeling of the compound with an isotope (e.g., $^{131}$I, $^{125}$I, Tc, Cr, $^3$H, etc.) or fluorochrome and injection of a known quantity of labeled compound intravascularly. Included are red blood cells (half life ca. 60 days), platelets (half life ca. 4–7 days), endothelial cells lining the blood vasculature, and long lived blood serum proteins, such as albumin, steroid binding proteins, ferritin, α2-macroglobulin, transferrin, thyroxin binding protein, immunoglobulins, especially IgG, etc. In addition to preferred half lives, the subject components are preferably in cell count or concentration sufficient to allow binding of therapeutically useful amounts of the compound of the present invention. For cellular long lived blood components, cell counts of at least 2,000/μl and serum protein concentrations of at least 1 μg/ml, usually at least about 0.01 mg/ml, more usually at least about 1 mg/ml, are preferred.

The selected cellular long lived blood components are present in high number in the vascular system. Platelets are present in from about $1$–$4 \times 10^5$/μl, while red blood cells are present in about $4$–$6 \times 10^6$/μl. The cells have a long half life and by appropriate preferential binding to a surface membrane protein, endocytosis is avoided. The erythrocyte and platelets lack a nucleus and cell division capability. Preferred cells have a wide distribution in capillaries and tissue and express specific binding sites on the cell surface associated with their specific differentiation. In addition to in vivo administration of the subject derivatized renin inhibitor, in the case of red blood cells and platelets, these cells may be readily collected, combined with the conjugate in vitro, and then administered to the host. The cells will normally be autologous or allogeneic, but in some instances may even be xenogeneic.

Suitable erythrocyte binding site containing molecules include glycophorin A, B and C, Band 3 and Rhesus blood group antigens. Preferred erythrocyte binding sites are abundantly expressed on the erythrocyte with copy numbers of at least 1,000, preferably at least 10,000, more preferably at least 100,000 per cell, desirably are tethered at least about 0.5, preferably at least about 1 nm above the bilayer surface and do not facilitate per se cell deformation when the conjugate is bound to the cell (e.g., the binding will be selected so as not to be a key component of the cytoskeleton). Binding sites of the erythrocyte surface glycoprotein glycophorin A and erythrocyte binding sites comprising sialic acid are examples of preferred binding sites. Preferred platelet binding sites include GPIIa, GPIIb, GPIIIa and GPIV. Desirably, upon binding to the target, deformation of the long-lived blood component, e.g. erythrocyte or platelet, does not occur.

The derivatized renin inhibitor compounds of the present invention will usually be administered as a bolus, but may be introduced slowly over time by infusion using metered flow, or the like. Alternatively, although less preferable, blood may be removed from the host, treated ex vivo, and supplied to the host. Blood components may also be isolated and treated with a derivatized renin inhibitor prior to administration. The derivatized renin inhibitor molecules will be administered in a physiologically acceptable medium, e.g. deionized water, phosphate buffered saline, saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The subject compositions will for the most part be administered parenterally, such as intravascularly (IV), intraarterially (IA), intramuscularly (IM), subcutaneously (SC), or the like. Administration will normally be by transfusion. In some instances, where reaction of the active functional group is relatively slow, administration may be oral, nasal, rectal, transdermal or aerosol, where the nature of the conjugate allows for transfer to the vascular system. Usually a single injection will be employed although more than one injection may be used, if desired. The derivatized renin inhibitor may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g. intravenously, peripheral or central vein. Other routes may find use where the administration is coupled with slow release techniques or a protective matrix. The intent is that the subject compound be effectively distributed in the blood, so as to be able to react with the blood components. The concentration of the conjugate will vary widely, generally ranging from about 1 pg/ml to 50 mg/ml.

For the most part, reaction will be with mobile components in the blood, particularly blood proteins and cells, more particularly blood proteins and red cells. By "mobile" is intended that the component does not have a fixed situs for any extended period of time, generally not exceeding 5, more usually one minute. Reaction will generally be with plasma proteins, such as the immunoglobulins particularly IgM and IgG, albumin, ferritin, and to a lesser degree other proteins which are present in substantially reduced amount. There may also be reaction with platelets, endothelial cells and white blood cells. There will therefore, initially be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

The manner of producing the derivatized renin inhibitor molecules of the present invention will vary widely, depending upon the nature of the various elements comprising said molecule. The synthetic procedures will be selected so as to be simple, provide for high yields, and allow for a highly purified product. Normally, the chemically reactive group will be created as the last stage, for example, with a carboxyl group, esterification to form an active ester will be the last step of the synthesis.

By binding to long-lived components of the blood, such as immunoglobulin, serum albumin, red blood cells and platelets, a number of advantages ensue. The inhibition of the renin is extended for days to weeks. Only one administration need be given during this period of time. Greater specificity can be achieved, since the active compound will be primarily bound to large molecules, where it is less likely to be taken up intracellularly to interfere with other physiological processes.

The following examples are offered by way of illustration and not by way of limitation.

EXAMPLE 1

Synthesis of a Derivatized Renin Inhibitor

Figure 5A:
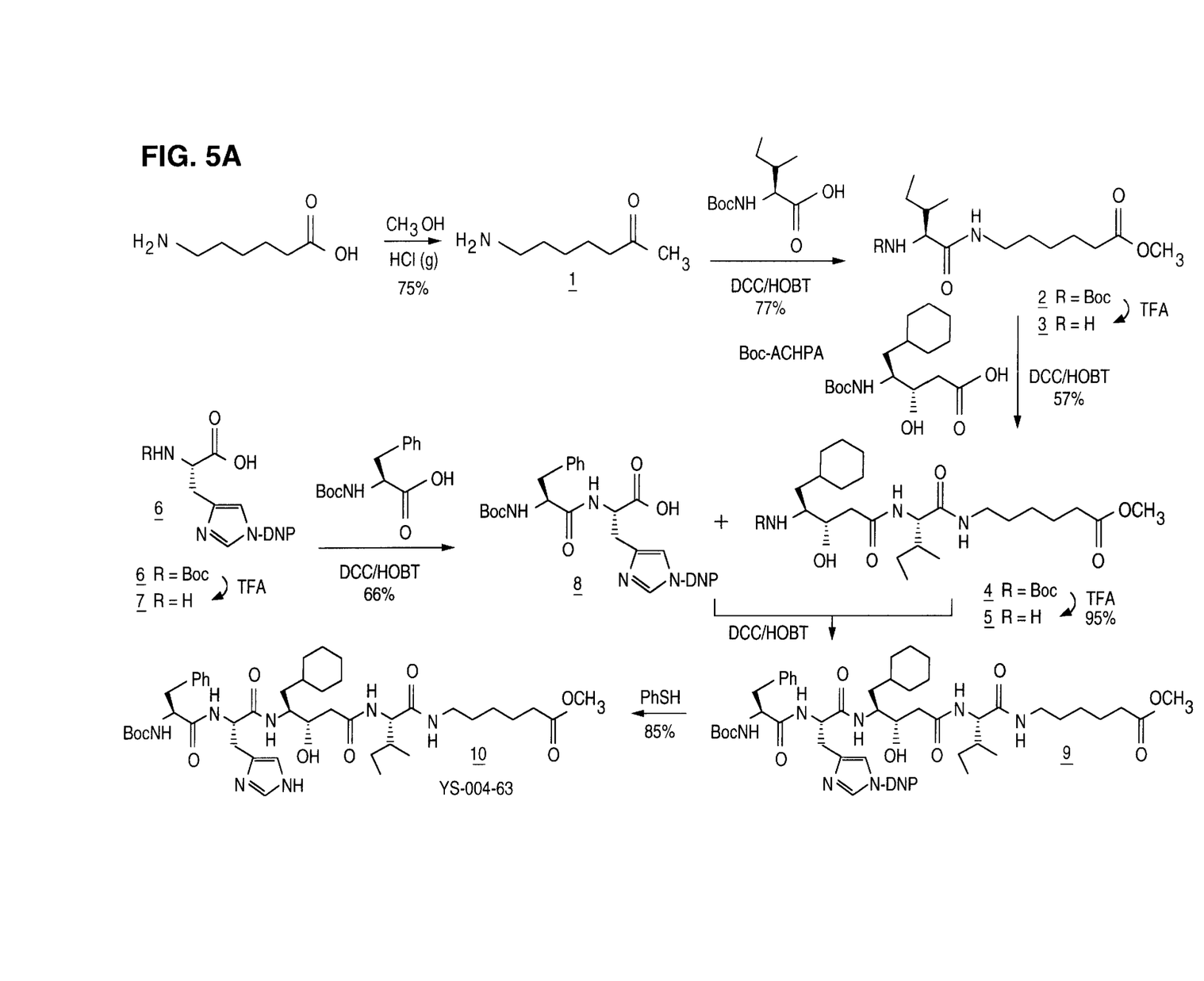
FIGS. 5A and 5B show a synthetic pathway describing the preparation of modified renin inhibitors.
Figure 5B:
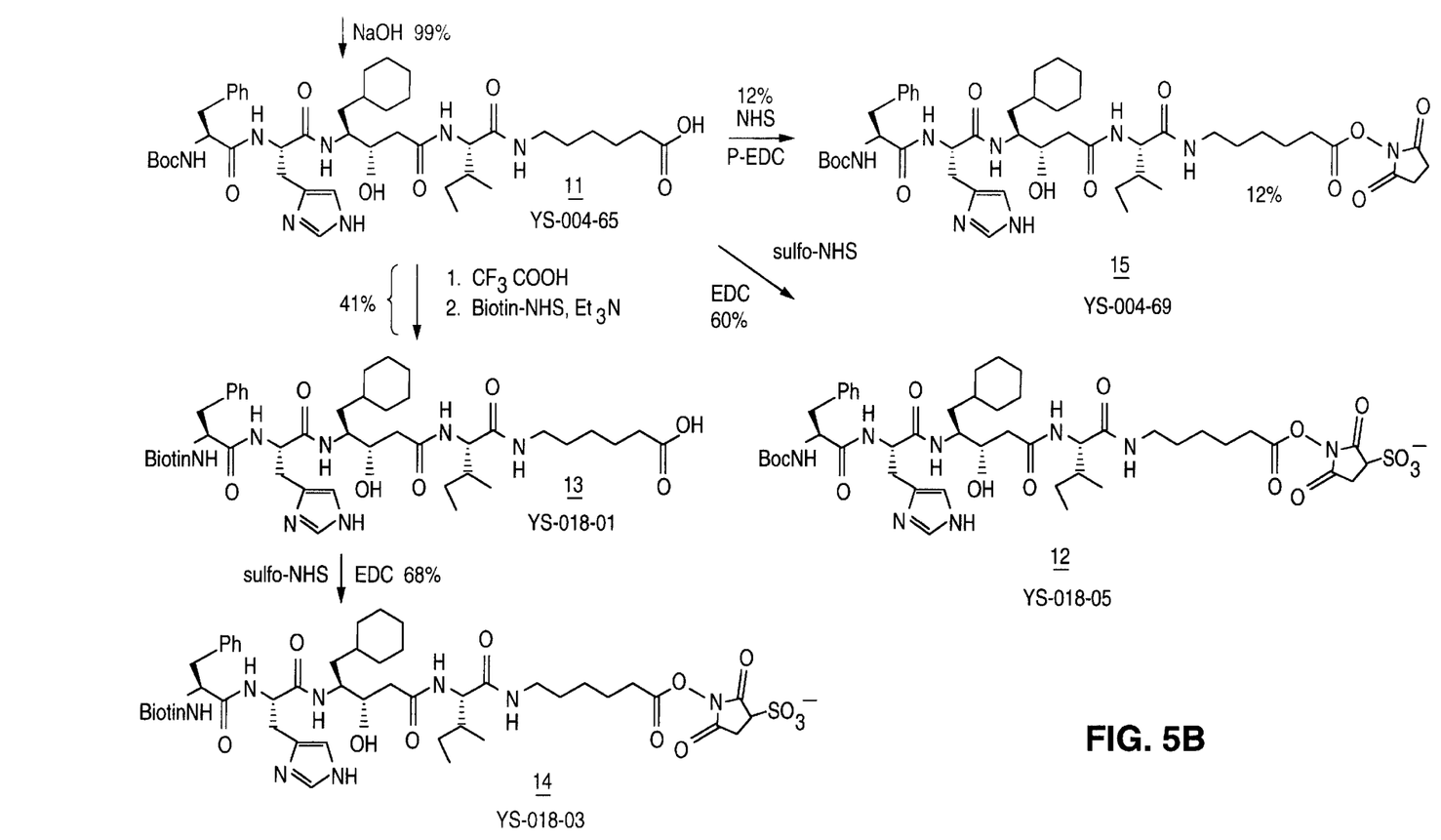

The numbers referred to in the following synthetic pathway are presented in FIGS. 5A and 5B.

Methyl 6-Aminocaproate (6-AC-OMe) Hydrochloride (YS-18-10) (1). To a suspension of 6-aminocaproic acid (3.00 g, 22.9 mmol) in anhydrous MeOH (60 mL), was introduced hydrogen chloride gas for 25 min., during which time the suspension became clear. The solution was then stirred at room temperature for 5 hours. MeOH was removed in vacuo. The residue was recrystallized from THF to give a white solid (1) (3.10 g). (Yield: 75%). The compound is better stored in hydrochloride form, because its free amino form tends to polymerize. $^1$HNMR (MeOH-d4, 300 MHz) δ 3.66 (s, 3H, OCH$_3$), 2.92 (t, 2H, J=7.7 Hz, NCH$_2$), 2.37 (t, 2H, J=7.2 Hz, CH$_2$CO$_2$), 1.74–1.60 (m, 4H, CH$_2$CH$_2$), 1.48–1.36 (m, 2H, CH$_2$).

Boc-Ile-6-AC-OMe (2) and H$_2$N-Ile-6-AC-OMe (3). To a solution of N-Boc isoleucine (2.55 g, 11.0 mmol) and HOBT (1.49 g, 11.0 mmol) in CH$_2$Cl$_2$ (250 mL) at 22° C., DCC (2.38 g, 11.6 mmol) was added. The mixture was stirred at 22° C. for 3 hour. A solution of methyl 6-aminocaproate hydrochloride (2.00 g, 11.0 mmol) and triethylamine (1.55 mL, 11.1 mmol) in anhydrous THF (25 mL) was added. The reaction mixture was then stirred at 22° C. overnight. The solvent was removed in vacuo. Ethyl ether was added, and the insoluble was filtered off. The ethereal solution was washed with 5% NaHCO$_3$, H$_2$O. It was then dried over Na$_2$SO$_4$, concentrated in vacuo to give an amorphous solid (2) (3.05 g) (yield: 77%). $^1$HNMR (300 MHz, CDCl$_3$) δ 6.00 (br. s, 1H, NH), 5.03 (br. s, 1H, NH), 3.86 (dd, 1H, J=8, 6 Hz, NCHCO), 3.68 (s, 3H, OCH$_3$), 3.32–3.20 (m, 2H, NCH$_2$CH$_2$), 2.32 (t, 2H, J=8 Hz, CH$_2$CO$_2$), 1.98–1.03 (m, 9H, CH$_2$), 1.45 (s, 9H, (CH$_3$)$_3$C), 0.96–0.84 (m, 6H, 2CH$_3$). MS (electrospray) 359.5 (M+H+), 717.7 (2M+H+) (358.2 calcd. for C$_{18}$H$_{34}$N$_2$O$_5$).

Boc-Ile-6-AC-OMe (3.00 g, 8.38 mmol) was dissolved in trifluoroacetic acid (30 mL). The solution was stirred at 22° C. for 2 hours. Trifluoroacetic acid was removed in vacuo. The residue was dissolved in a minimum amount of THF, H$_2$O was added. The solution was then lyophilized to give an oil (3) (3.11 g) (yield: 99%).

Boc-ACHPA-Ile-6-AC-OMe (4) and H$_2$N-ACHPA-Ile-6-AC-OMe (5). To a solution of Boc-ACHPA (2.64 g, 8.38 mmol) and HOBT (1.24 g, 9.19 mmol) in CH$_2$Cl$_2$ (80 mL) at 22° C., DCC (1.89 g, 9.17 mmol) was added. The solution was stirred at 22° C. for 4 hours. A solution of H$_2$N-Ile-6-AC-OMe (3.11 g, 8.37 mmol) and triethylamine (2.32 mL, 16.7 mmol) in CH$_2$Cl$_2$ (30 mL) was added. The reaction mixture was stirred at 22° C. overnight. The precipitates were filtered off, and the filtrate was washed with 5% NaHCO$_3$ twice, then with H$_2$O. The solution was dried over Na$_2$SO$_4$, concentrated in vacuo to give a solid residue, which was purified by a flash silica gel column using solvents ethyl acetate/hexane (70/30) to give a white amorphous solid (4) (2.66 g) (yield: 57%). $^1$HNMR (300 Mhz, CDCl$_3$) δ 6.48 (d, 1H, J=10 Hz, NH), 6.39 (br.t, 1H, J=5 Hz, NHCH$_2$), 4.76 (d, 1H, J=10 Hz, NH), 4.26 (dd, 1H, J=10, 8 Hz, a-H of Ile), 4.04–3.93 (br.m, 1 H, CHOH), 3.75 (d, 1 H, J=3 Hz, OH), 3.66 (s, 3H, OCH$_3$), 3.65–3.53 (br.m, 1 H, NCHCHOH), 3.25 (dt, 2H, J=5, 6 Hz, NCH$_2$CH$_2$), 2.55–2.41 and 2.39–2.23 (m, 2H, HOCHCH$_2$CO), 2.30 (t, 2H, J=8 Hz, CH$_2$CO$_2$), 1.98–1.03 (m, 19H), 1.46 (s, 9H, (CH$_3$)$_3$C), 1.02–0.7 (m, 9H).

Boc-ACHPA-Ile-6-AC-OMe (4) (2.64 g, 4.76 mmol) was dissolved in trifluoroacetic acid (35 mL). The solution was stirred at 22° C. for 2 hours. Trifluoroacetic acid was removed in vacuo. The residue was dissolved in ethyl acetate (150 mL). The solution was washed with 5% NaHCO$_3$ three times, then with H$_2$O. It was dried over Na$_2$SO$_4$, concentrated in vacuo to give a solid (5) (2.05 g) (yield: 95%).

Boc-Phe-DNP-His (8). Boc-DNP-His (6) (contains 1 mol of isopropanol, 6.69 g, 13.9 mmol) was dissolved in trifluoroacetic acid (40 mL). The solution was stirred at 22° C. for 1 hour. Trifluoroacetic acid was removed in vacuo. The residue was dissolved in H$_2$O (40 mL), and it was lyophilized to give a greenish solid (H$_2$N-DNP-His) (7).

To a solution of Boc-Phe (3.68 g, 13.9 mmol) and HOBT (1.88 g, 13.9 mmol) in CH$_2$Cl$_2$ (100 mL) at 22° C., DCC (2.88 g, 14.0 mmol) in CH$_2$Cl$_2$ (30 mL) was added. The reaction mixture was stirred at 22° C. for 5 hours. The precipitates were filtered off, and the filtrate was concentrated in vacuo. To the residue, a solution of H$_2$N-DNP-His prepared above in anhydrous DMF (80 mL) was added, followed by addition of triethylamine (5.80 mL, 41.7 mmol).

The reaction mixture was then stirred at 22° C. overnight. Water and ethyl acetate were added. The organic layer was separated, and the aqueous layer was extracted with ethyl acetate once more. The combined organic phases were extracted with 5% NaHCO$_3$. To the NaHCO$_3$ solution, 6N HCl was added to adjust the pH to 2 to 3. The product was then extracted with ethyl acetate. The ethyl acetate solution was dried over Na$_2$SO$_4$, concentrated in vacuo to give a yellowish powder (8) (5.18 g) (yield: 66%).

Boc-Phe-DNP-His-ACHPA-Ile-6-AC-OMe (9). To a solution of Boc-Phe-DNP-His (2.55 g, 4.49 mmol) and HOBT (0.606 g, 4.49 mmol) in CH$_2$Cl$_2$ (60 mL), DCC (0.943 g, 4.58 mmol) was added. The solution was stirred at 22° C. for 1 hour. A solution of H$_2$N-ACHPA-Ile-6-AC-OMe (2.04 g, 4.48 mmol) in CH$_2$Cl$_2$ (15 mL) was added. The mixture was then stirred at 22° C. overnight. The precipitates were filtered off. The filtrate was washed with 5% NaHCO$_3$, then H$_2$O. It was dried over Na$_2$SO$_4$, concentrated in vacuo to give a yellow solid (3.97 g), which could be used without further purification. For a pure sample, it (108 mg) could be purified on a flash silica gel column using solvents CH$_2$Cl$_2$/MeOH (95/5) to afford a yellowish solid (9) (78 mg).

Boc-Phe-His-ACHPA-Ile-6-AC-OMe (10). To a solution of Boc-Phe-DNP-His-ACHPA-Ile-6-AC-OMe (0.540 g, 0.537 mmol) in DMF (8 mL), thiophenol (1.35 mL, 13.2 mmol) was added. The mixture was stirred at 22° C. overnight. The solution was concentrated in vacuo. The residue was applied to a silica gel column, which was then eluted first with CH$_2$Cl$_2$ to remove the relatively non-polar components, then with CH$_2$Cl$_2$/MeOH/NH$_3$ (95/5/1). The positive fractions were pooled, concentrated in vacuo to give a brownish solid (10) (0.385 g) (yield: 85%).

Boc-Phe-His-ACHPA-Ile-6-AC-OH (11). To a solution of Boc-Phe-His-ACHPA-Ile-6-AC-OMe (0.180 g, 0.215 mmol) in THF (4 mL), 1N NaOH (1.0 mL) was added. The mixture was stirred at 22° C. overnight. Water (10 mL) was added. THF was removed in vacuo to give a cloudy solution, which was acidified with 1N HCl to pH 2 to 3. The product was extracted with ethyl acetate three times. Each time, efforts were made to dissolve the light white precipitates (presumably the sodium salt of the free carboxylic acid). The combined ethyl acetate solutions were dried over Na$_2$SO$_4$, concentrated in vacuo to give a solid (11) (0. 175 g) (yield: 99%).

Boc-Phe-His-ACHPA-Ile-6-AC-sulfo-NHS (12). To a solution of Boc-Phe-His-ACHPA-Ile-6-AC-OH (147 mg, 0.178 mmol) and sulfo-NHS (77 mg, 0.36 mmol) in anhydrous DMF (5 mL), EDC (102 mg, 0.532 mmol) was added. The solution was stirred at 22° C. overnight. The solution was filtered, and concentrated in vacuo. The residue was washed with H$_2$O twice to remove excess of EDC and sulfo-NHS. After being dried on vacuum, the residue was dissolved in methanol (5 mL), H$_2$O (20 mL) was added to induce precipitation. The precipitates were collected, washed with H$_2$O, dried on vacuum to give a solid (12) (109 mg) (yield: 60%).

N-Biotin-Phe-His-ACHPA-Ile-6-AC-OH (13). A solution of Boc-Phe-His-ACHPA-Ile-6-AC-OH (40 mg, 49 μmol) in anhydrous trifluoroacetic acid (2 mL) was stirred at 22° C. for 3 hours. Trifluoroacetic acid was removed in vacuo. The residue was dissolved in minimum amount of methanol, H$_2$O was added. The solution was then lyophilized to give a powder (44 mg). It was dissolved in anhydrous DMF (3 mL). To the solution, triethylamine (20 μL, 144 μmol) was added, followed by addition of biotin-NHS (17.6 mg, 51.5 μmol). The mixture was heated to 60° C. and was stirred at that temperature for 5 hours. DMF was removed in vacuo. The residue was dissolved in methanol (1 mL), H$_2$O (15 mL) was added to induce precipitation. The precipitates were collected and dried on vacuum to give a powder (13) (19 mg) (yield: 41%)

N-Biotin-Phe-His-ACHPA-Ile-6-AC-sulfo-NHS (14). To a solution of N-Biotin-Phe-His-ACHPA-Ile-6-AC-OH (9.8 mg, 10 μmol) and sulfo-NHS (4.5 mg, 21 μmol) in anhydrous DMF (400 μL), EDC (5.9 mg, 31 μmol) was added. The mixture was stirred at 22° C. overnight. DMF was removed in vacuo. The residue was washed with H$_2$O twice to remove excess of EDC and sulfo-NHS. It was dried on vacuum to give a solid (14) (8 mg) (yield: 68%).

Boc-Phe-His-ACHPA-Ile-6-AC-NHS (15). To a mixture of P-EDC (555 mg, 0.63 meq/g, 350 μmol), Boc-Phe-His-ACHPA-Ile-6-AC-OH (90 mg, 109 μmol) and NHS (25 mg, 17 μmol) in a sintered glass syringe tube, anhydrous DMF (6 mL) was added. After the substances were dissolved, CHCl$_3$ (6 mL) was added. The suspension was agitated by a stream of N$_2$ at 22° C. overnight. The solution was filtered, and the resin was washed with DMF. The combined filtrates were concentrated in vacuo. The residue was purified by HPLC on a C18 column using a gradient of 10–70% CH$_3$CN in H$_2$O (containing 0.45% TFA) over 45 min, to afford a solid (15) (12 mg) (yield: 12%).

Additional derivatized renin inhibitors with different length linker groups may be synthesized by the above procedure by substituting linker groups of various lengths in the synthetic pathway.

EXAMPLE 2

The Half-Life of a Derivatized Renin Inhibitor is Extended More than 200-fold on Rabbit Erythrocytes Material and Methods: Fresh rabbit blood was collected on heparin. Cells were separated from plasma by centrifugation at 2500 rpm. The cells were washed three times with sterile phosphate buffered saline (PBS), pH 7.4. One set of cells was resuspended to 10% in PBS and gently rocked with 21 μM YS-004-39 (biotin-tagged, C11 linked renin inhibitor; see FIG. 2) for 15 minutes at room temperature. Additional equivalent aliquots of YS-004-39 were added for two sequential labeling periods. The final DMSO concentration was 0.62%.

Unreacted or hydrolyzed starting material was removed by centrifugation and three successive washes of the cells with PBS. Aliquots of labeled cells were subjected to membrane protein extraction and then these proteins were subsequently resolved and analyzed by SDS-PAGE and immunoblotting which confirmed the covalent modification of erythrocyte membrane proteins with the biotinylated renin inhibitor YS-004-39. These cells, as well as a second batch of erythrocytes, were then labeled with a commercially available green fluorescent tag (FITC) in order to trace the cells after their return to rabbits. The final DMSO concentration during the FITC labeling was 0.1%.

After labeling, excess reagent was removed by extensive washing with PBS. The final cell pellet was resuspended to 50% in autologous plasma. These two suspensions were then intravenously injected into two autologous rabbits. The rabbits were bled at defined intervals and erythrocytes were harvested from each sample of fresh blood. A red fluorescent tag, phycoerythrin conjugated avidin, was used to monitor the lifetime of the biotinylated renin inhibitor-modified erythrocytes (bRI-RBC).

Figure 3:
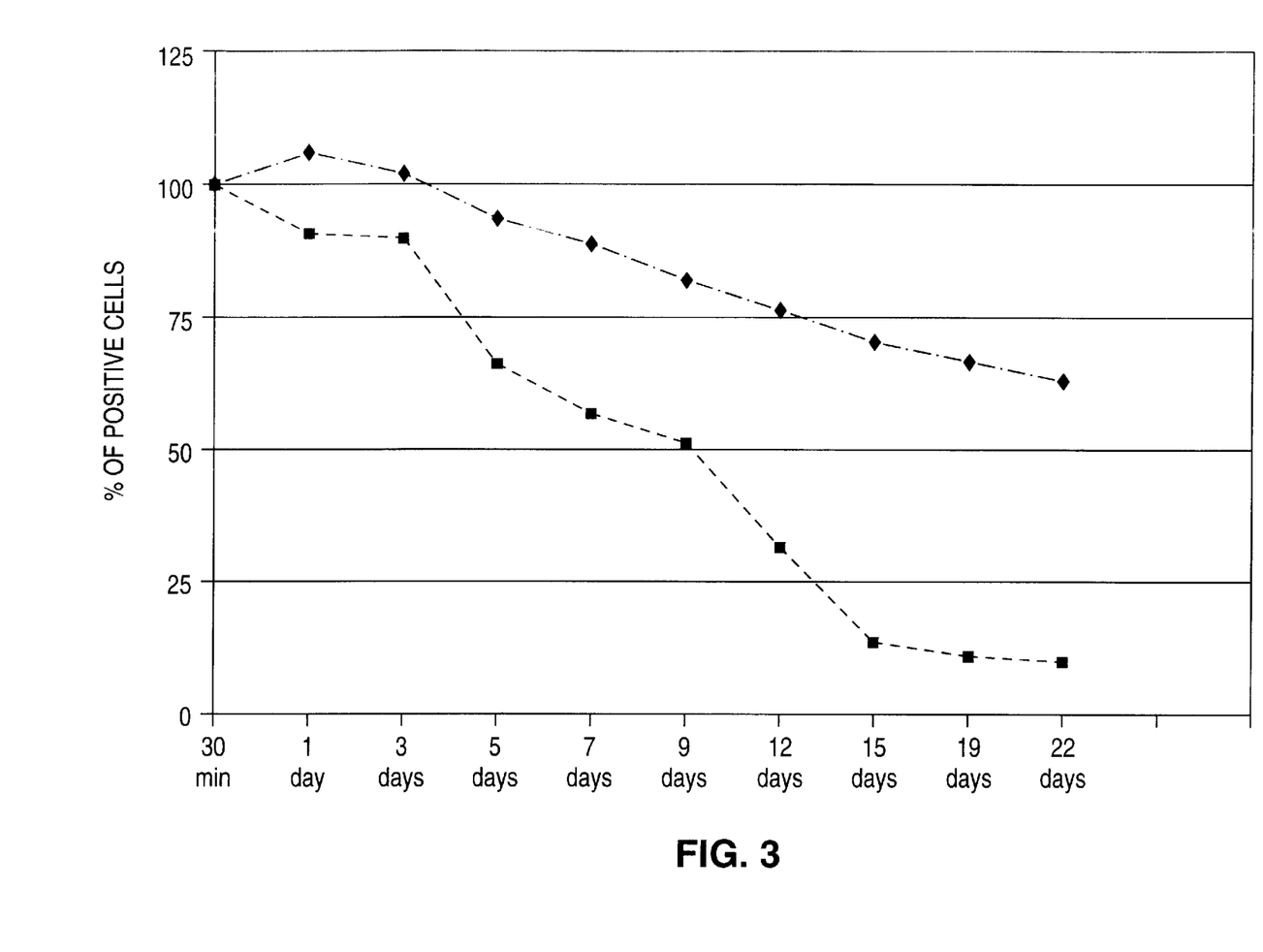
FIG. 3 is a graph showing the lifetime of derivatized cells. Data is presented showing the percent of positively derivatized cells ("% of positive cells") versus time.

Results: Erythrocytes were analyzed by flow cytometry and the number of fluorescently-tagged cells was calculated using a software program within the fluorometer. The starting population of FITC-labeled cells in each rabbit was found to be 7%. This starting value of labeled cells was used to normalize all later time points in order to control for the dilution, both in number and in fluorescence intensity, of the labeled cells by the non-labeled cells. FIG. 3 illustrates the number of labeled cells remaining at different time points after injection into the rabbit. The half-life for the FITC-tagged erythrocytes was found to be greater than 22 days, while that for the bRI/FITC-labeled erythrocytes was 9 days. The lifetime of the FITC tag is superimposable on the lifetime curve established for the biotin tag on the bRI/FITC-labeled erythrocytes.

In other experiments, erythrocytes were labeled with YS-004-39 alone. The average half-life for these bRI-RBCs is 7.5 days. Without the attachment to erythrocytes, this family of renin inhibitors is cleared from the blood stream within 60 minutes. Therefore, the delivery of this drug via a red blood cell has extended the lifetime of the drug by alniost two hundred-fold.

EXAMPLE 3

Determination of Immunogenicity

The average half-life of a rabbit erythrocyte is 25–30 days. The half-life of cells labeled with FITC alone approached this normal range. The half-life of the cells which were doubly labeled with FITC and biotinylated renin inhibitor was 7.5 days. There are several explanations, occurring singly or in combination, which might contribute to this shortened lifetime. First, the double-labeled cells undergo several manipulations in higher DMSO concentrations than the FITC-labeled cells. These additional manipulations alone may have resulted in a shortened half-life. Second, the presence of a renin inhibitor, albeit with a high $IC_{50}$, may have resulted in the accelerated clearance of these modified cells as compared to unlabeled cells. Lastly, an immune response may have been initiated by the modified erythrocytes, which then resulted in their clearance from the bloodstream. A set of experiments was conducted to test for this latter possibility.

Material and Methods: A conjugate of bovine serum albumin (BSA) and the renin inhibitor (YS-004-69; see FIG. 2) was prepared and then coated onto ELISA plates. Plasma was prepared from one of the rabbits described in Example 2 above on various days post introduction of bRI(YS-004-39)-labeled erythrocytes. The plasma was titered neat or diluted 1:10 on the plate. Binding of rabbit antibodies was detected by HRP-tagged goat anti-rabbit Ig antibodies. The plasma was also assayed by flow cytometry for its ability to stain a fresh preparation of bRI-labeled erythrocytes.

Figure 4:
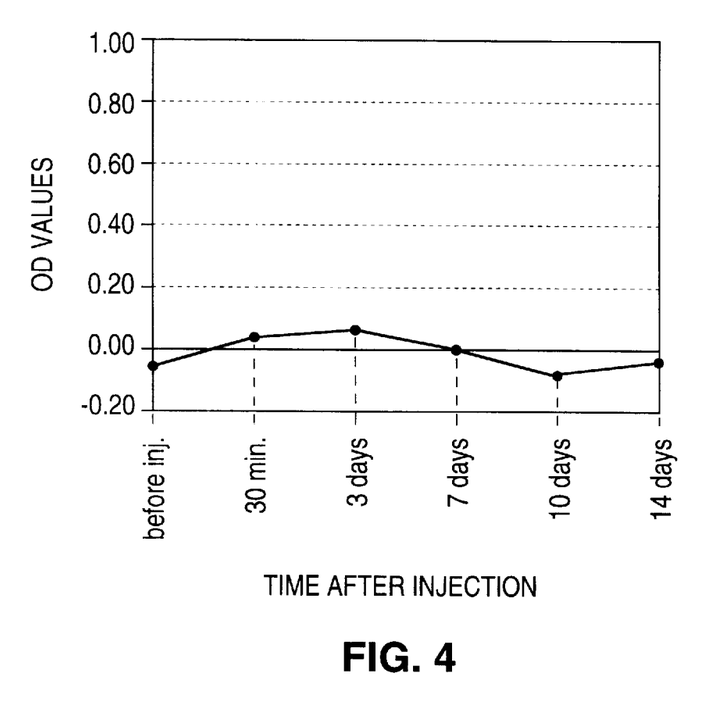
FIG. 4 is a graph showing the immunogenicity of a covalently bound renin inhibitor up to 14 days post-injection. "OD values" is a measure of the amount of antibody directed against the covalently-bound renin inhibitor.

Results: As is shown in FIG. 4, by ELISA, no antibodies specific for the renin inhibitor were detected in plasma obtained from the rabbit tested. In addition, this plasma did not stain bRI-labeled erythrocytes (data not shown), also suggesting anti-RI antibodies were not generated.

Example 4

Bio activity of Renin Inhibitor Derivatives

Figure 1:
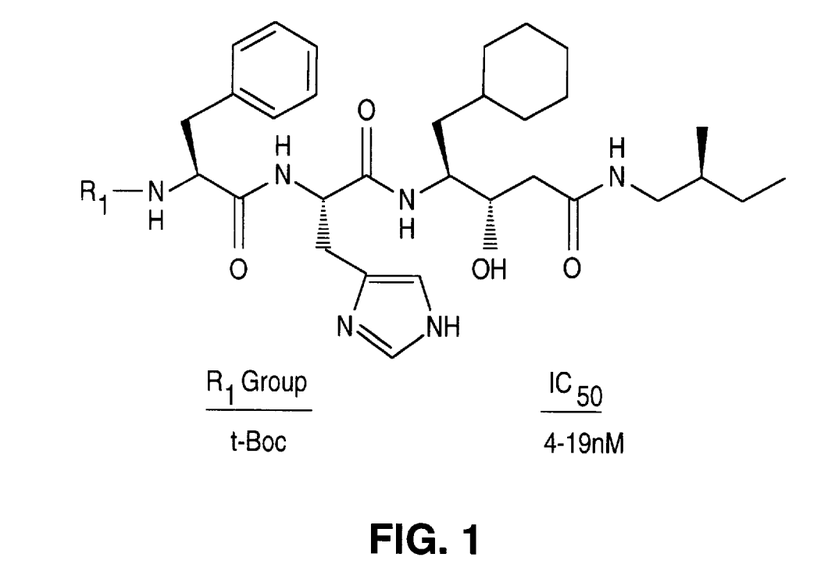
FIG. 1 shows the formula of the parent renin inhibitory compound upon which the derivatized renin inhibitor compounds of the present invention are based and the relative activity of the parent compound. "t-Boc" is t-butyloxycarbonyl.
Figure 2:
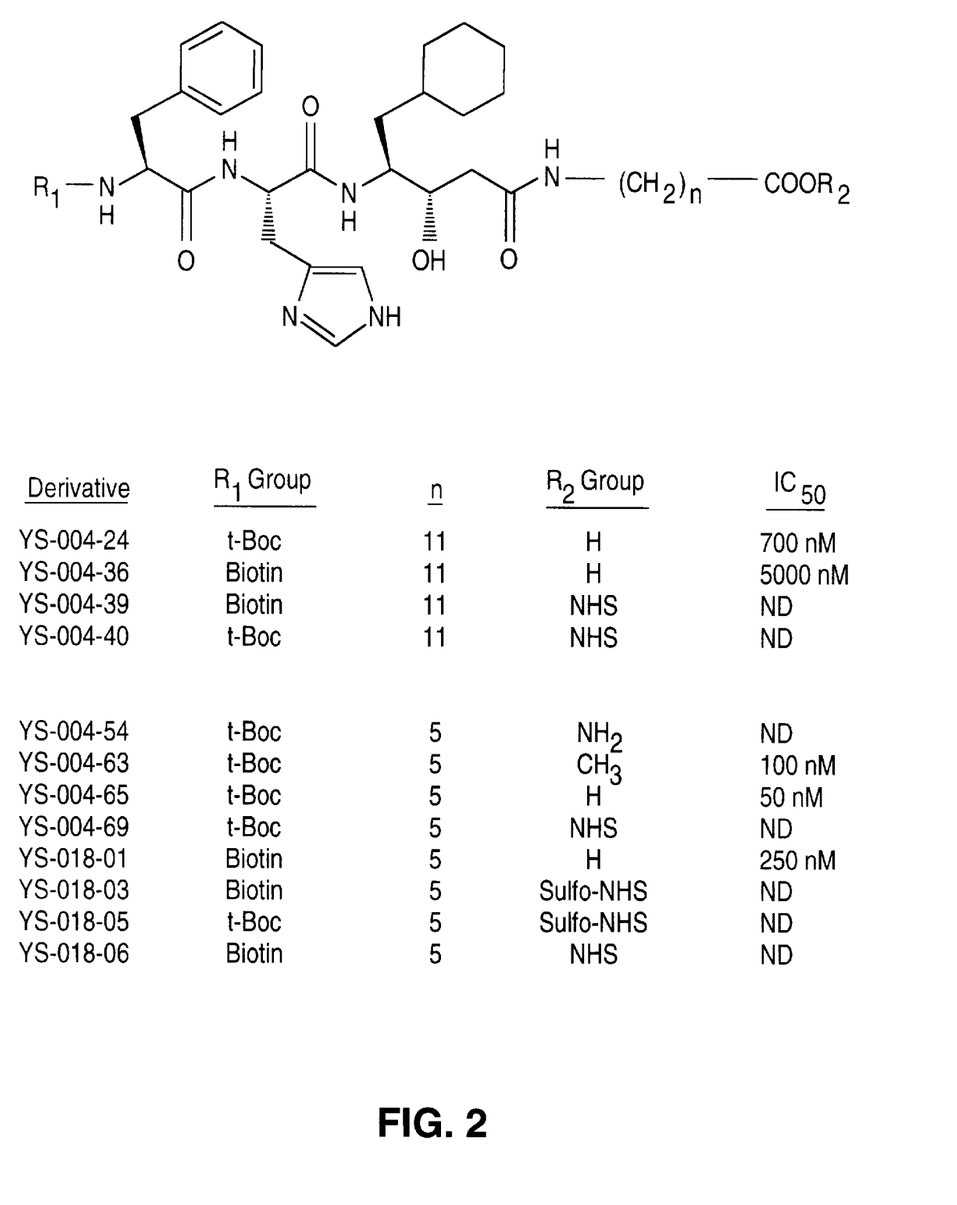
FIG. 2 shows the formulae of various derivatized renin inhibitor compounds according to the subject invention and their biological activity. "t-Boc" is t-butyloxycarbonyl. "NHS" is the acylating group N-hydroxysuccinimide. "Sulfo-NHS" is N-hydroxy sulfosuccinimide. "ND" means that this measurement was not determined.

The information presented above clearly demonstrates that the biotin ring on the renin inhibitor (YS-004-39 (15); see FIG. 2) is accessible for binding to avidin. The next series of experiments was designed to address whether compound YS-004-69 (see FIG. 2), which has an $IC_{50}$ of 50 nM in its soluble free acid form (YS-004-65; FIG. 2), is still bioactive after conjugation to target proteins.

Materials and Methods: The following procedures were done under sterile conditions. Rabbit plasma was obtained from freshly drawn heparinized blood. One 8 mL aliquot of plasma was incubated with 5 micromoles of YS-004-69 (15) (the NHS ester; "NHS-RI") for 60 minutes at room temperature. Another equal aliquot was similarly incubated with 5 micromoles of YS-004-65 (free acid; "Free RI"). The reaction mixtures were stored at 4° C. overnight. Aliquots of these samples were saved for analysis of total renin inhibitor content by a standard renin radioimmunoassay (RIA). After warming to 37° C., the plasma samples were injected into two autologous rabbits. The rabbits were then bled at defined intervals. The blood was centrifuged for 5 minutes at 2500 rpm and then aliquots of the plasma were analyzed by RIA.

Results: Plasma proteins derivatized with the NHS ester of the renin inhibitor did indeed maintain the inhibitor in a conformation which remained bioavailable and inhibitory after an extended period of circulation in the blood. Table 1 shows the results obtained when measuring the amount of renin inhibitor detectable in the plasma by RIA versus the time of the bleed after the initial injection of plasma. Again, the amount of inhibitor detectable has been normalized for the effect of dilution of the plasma by the volume of blood in circulation. "ND" means this measurement was not determined.

TABLE 1

| Time After Injection | Crude % Inhibition | | Corrected % Inhibition | |
|---|---|---|---|---|
| | Free RI | NHS-RI | Free RI | NHS-RI |
| 10 min | 89.40 | 97.70 | 100.00 | 100.00 |
| 30 min | 20.60 | 87.40 | 23.04 | 89.46 |
| 1 hour | −2.80 | 85.90 | −3.13 | 87.92 |
| 4 hours | −5.20 | 87.40 | −5.82 | 99.69 |
| 6 hours | −0.40 | 88.20 | −0.45 | 100.51 |
| 8 hours | −2.90 | 70.50 | −3.24 | 72.16 |
| 1 day | −5.20 | 75.10 | −5.82 | 76.87 |
| 2 days | −3.20 | 68.10 | −3.58 | 69.70 |
| 3 days | 1.40 | 75.80 | 1.57 | 77.38 |
| 6 days | ND | 55.30 | 0.00 | 56.60 |
| 10 days | −6.60 | 41.20 | −7.38 | 42.17 |

As is shown in Table 1, the level of free acid of the renin inhibitor falls rapidly and is not detectable after one hour. On the other hand, the NHS-ester-modified plasma proteins are inhibitory in the renin assay, indicating that the derivatization did not destroy the bioactivity of the inhibitor. Furthermore, the level of the inhibition observed does not significantly decrease until day 10. Several abundant plasma proteins (albumin and immunoglobulins) are long-lived and could account for this delivery profile. These results, therefore, clearly demonstrate that covalent attachment of a derivatized renin inhibitor to plasma proteins does not destroy the bioactivity of the molecule and significantly increases the lifetime of the inhibitor in the blood.

It is evident from the above results that the subject invention provides for greatly improved treatment involving renin inhibition. By use of the subject invention, the renin inhibitors maintain for extended periods of time, so that repetitive dosages are not required, compliance by the patient is not required, and protection is ensured. The derivatized renin inhibitors of the present invention covalently attach to erythrocytes, plasma proteins and various other vascular components while retaining biological activity and are not immunogenic.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A compound of the formula:

wherein:
- $R_1$ is an acyl group or alkoxy carbonyl group of 1–10 carbon atoms, or biotin;
- Y is a linking group of from 2–30 atoms;
- Z is a chemically reactive group for reacting with a reactive functionality of a target molecule in an aqueous system to form covalent bonds therewith or a precursor to said chemically reactive group;
- a is 0 or 1;

and wherein said compound possesses renin inhibitory activity in vivo.

2. The compound according to claim 1 wherein $R_1$ is an alkoxy carbonyl group selected from the group consisting of t-butoxycarbonyl and methoxyacetyl.

3. The compound according to claim 1 wherein said acyl group is selected from the group consisting of formyl, acetyl, propionyl and butyryl.

4. The compound according to claim 1 wherein $R_1$ is biotin.

5. The compound according to claim 1 wherein Y is an alkylene, oxyalkylene or polyoxyalkylene group.

6. The compound according to claim 5 wherein said oxyalkylene group has from 2–3 carbon atoms.

7. The compound according to claim 1 wherein Y has 11 atoms.

8. The compound according to claim 1 wherein Y has 5 atoms.

9. The compound according to claim 1 wherein Z is a carboxy group, a carboxy ester group or a mixed anhydride.

10. The compound according to claim 9 wherein Z is selected from the group consisting of N-hydroxysuccinimide, N-hydroxy sulfosuccinimide, maleimide-benzoyl-succinimide, gamma-maleimido-butyryloxy succinimide ester, maleimidopropionic acid, N-hydroxysuccinimide, isocyanate, thiolester, thionocarboxylic acid ester, imino ester, carbodiimide anhydride and carbonate ester.

11. A composition comprising the compound of claim 1 and a physiologically acceptable carrier.

12. A method for inhibiting renin activity in vivo, said method comprising:

introducing into the bloodstream of a mammalian host a compound according to claim 1 in an amount sufficient to provide an effective amount for renin inhibition;

whereby said compound reacts with and becomes covalently bound to long lived blood components and renin inhibition is maintained over an extended period of time as compared to the lifetime of unbound renin inhibitor.

13. A method for inhibiting renin activity in a host, said method comprising:

a) treating blood ex vivo with a compound according to claim 1 for a time sufficient for said compound to covalently bond to one or more long lived blood components of said blood to form treated blood, and b) administering said treated blood to said host.

14. A method for inhibiting renin activity in a host, said method comprising:

a) treating one or more blood proteins ex vivo with a compound according to claim 1 for a time sufficient for said compound to covalently bond to one or more of said proteins to form one or more modified proteins; and b) administering said modified protein or proteins to said host.

15. The method of claim 14 wherein said blood protein is serum albumin.

* * * * *